(12) United States Patent
Ingles, Jr. et al.

(10) Patent No.: US 6,937,325 B2
(45) Date of Patent: Aug. 30, 2005

(54) METHOD AND APPARATUS FOR MEASURING ECCENTRICITY IN A OPTICAL FIBER

(75) Inventors: Andrew Ingles, Jr., Alpharetta, GA (US); Albert Ritger, Lawrenceville, GA (US); Zhi Zhou, Lawrenceville, GA (US); Harry D. Garner, Lawrenceville, GA (US)

(73) Assignee: Fitel U.S.A. Corporation, Norcross, GA (US)

( * ) Notice: Subject to any disclaimer, the term of this patent is extended or adjusted under 35 U.S.C. 154(b) by 63 days.

(21) Appl. No.: 10/354,277

(22) Filed: Jan. 30, 2003

(65) Prior Publication Data

US 2004/0150811 A1 Aug. 5, 2004

(51) Int. Cl.[7] .............................................. G01N 21/00
(52) U.S. Cl. ..................................................... 356/73.1
(58) Field of Search ....... 356/73.1; 250/559.42–559.45, 250/559.4; 65/486, 377, 488, 381, 491, 382

(56) References Cited

U.S. PATENT DOCUMENTS 4,882,497 A  * 11/1989 Inoue et al. ........... 250/559.08
5,943,466 A    8/1999 Henderson et al.
6,020,584 A    2/2000 Brarens et al.

FOREIGN PATENT DOCUMENTS

JP          2001013034         1/2001
JP          11-176205        * 12/2001

OTHER PUBLICATIONS

MJ Marrone et al.; "Internal rotation of the birefringence axes in polarization–holding fibers"; Optics Letters; 1987; vol. 12, No. 1; pp. 60–62.

* cited by examiner

Primary Examiner—Tu T. Nguyen
(74) Attorney, Agent, or Firm—Gardner Groff, P.C.

(57) ABSTRACT

A method and an apparatus for obtaining measurements of eccentricity in optical fibers, from which the spin imparted to the optical fiber can be ascertained. The method and apparatus enable eccentricity to be measured in such a way that this measurement can be utilized to determine the amount of spin imparted to an optical fiber as the optical fiber was being drawn, although the eccentricity measurement may be used for purposes other than to determine the amount of spin in the fiber. By viewing the fiber from one or more positions along the length of the fiber, the eccentricity of the fiber as a function of position along the length of the fiber can be determined. The amount of spin in the fiber can then be determined from the eccentricity measurement.

21 Claims, 5 Drawing Sheets

METHOD AND APPARATUS FOR MEASURING ECCENTRICITY IN A OPTICAL FIBER

TECHNICAL FIELD OF THE INVENTION

The present invention is generally related to the field of fiber optics, and, more particularly, to measuring eccentricity in an optical fiber.

BACKGROUND OF THE INVENTION

Optical fiber used in communication systems typically includes a glass core surrounded by a cladding that is also formed from glass. The glass cladding and the glass core have different optical properties. Typically, one or more protective coating layers surround the core and cladding. Such fibers can be made by drawing a thin strand from a heated, partially molten glass preform having the proper composition to cause the cladding surrounding the core to have the proper composition. As a strand of soft, molten glass is pulled from the preform, both the core glass and the cladding glass stretch. During this process, the core remains in the middle of the fiber and the cladding remains on the outside, thus forming the composite core and cladding structure of the finished fiber. As the fiber is pulled away from the preform, it cools and solidifies, and the coating is applied. These processes normally are performed at high speeds so that the fiber is drawn at high rates.

In optical fiber communications systems, light injected into one end of the fiber is pulsed, or progressively varied, in accordance with information to be transmitted over the system. The speed at which light propagates along a fiber depends upon many factors, including the optical properties of the materials that make up the core and cladding and the diameter of the core. Light passing along the fiber typically includes portions of light having different polarizations, i.e., different orientations of the electromagnetic waves constituting the light. If the fiber core is not perfectly cylindrical, but instead has long and short diameters, light of one polarization will have its electrical waves aligned with a long diameter of the core whereas light of another polarization will have its electrical waves aligned with the short diameter of the core. In this case, the effective diameter of the fiber core will be different for light of one polarization than for light of another polarization. Portions of light having different polarizations will travel at different velocities. In addition to this geometrical effect, differential thermal expansion between the core and cladding gives rise to stress induced birefringence, which also increases the difference between propagation velocities of light of different polarizations. Stated another way, the fiber has a "slow" axis in one direction perpendicular to its length, and a "fast" axis in the other direction perpendicular to its length.

Light having a direction of polarization aligned with the fast axis travels more rapidly than light having a direction of polarization aligned with the slow axis. As a result, the two polarization modes propagate with different propagation constants. The difference between the propagation constants is termed birefringence, and the magnitude of the birefringence is given by the difference between the propagation constants of the two orthogonal modes. Birefringence causes the polarization state of light propagating in the fiber to evolve periodically along the length of the fiber. The distance required for the polarization to return to its original state is typically referred to as the fiber beat length, which is inversely proportional to the fiber birefringence. Accordingly, fibers with more birefringence have shorter beat lengths, and vice versa.

In addition to causing periodic changes in the polarization state of light traveling in a fiber, the presence of birefringence means that the two polarization modes travel at different group velocities, with the difference increasing as the birefringence increases. The differential time delay between the two polarization modes is called polarization mode dispersion, or PMD. Imperfections in the fiber other than core shape can also contribute to PMD. PMD distorts the light pulses or waves transmitted along the fiber, thus reducing the signal quality and limiting the rate at which information can be passed along the fiber. PMD is very harmful to signal quality for high bit rate systems and analog communication systems.

One way to reduce the effects of PMD is to continually re-orient the fast and slow axes of the fiber. This can be accomplished by spinning the fiber as it is drawn so that the slow axis and the fast axis of the fiber are repeatedly interchanged along the length of the fiber. Thus, at one point along the length of the fiber the slow axis points in a first direction perpendicular to the length of the fiber and the fast axis points in a second direction perpendicular to the length of the fiber and to the first direction. At another point along the length of the fiber, the fast axis points in the first direction and the slow axis points in the second direction. The specifics regarding reduction in PMD achieved by spinning the fiber depend on the detailed variation of the orientation of the fast and slow axes along the length of the fiber, and so it is often desired to have a particular pattern of spin imposed along the length of a fiber.

Therefore, the manner in which fiber is spun during the drawing process should be monitored because, for various reasons, at times the device that spins the fiber malfunctions or performs improperly. The spin device is located on the draw tower and some spin devices are variable so that if a determination is made that the amount of spin is improper, the spin device can be adjusted to correct the spin. A known technique for measuring the spin in the fiber generally utilizes polarization characteristics of a length of fiber being tested to measure spin. The known method couples polarized light into a short length of fiber (e.g., two meters) and aligns a polarizer on one end of the piece of fiber with a polarization adjuster on the other end. A particular length of the fiber is cut off (e.g., one centimeter), the polarizer and the polarization analyzer are realigned and the angle of the polarization analyzer is recorded. The angular position of the polarization analyzer is directly related to the spin fixed in the glass. The process is very slow and would appear to be impractical to automate.

Accordingly, a need exists for a method and apparatus for accurately measuring the spin in an optical fibers.

SUMMARY OF THE INVENTION

The present invention provides a method and an apparatus for obtaining measurements of eccentricity in optical fibers, from which the spin imparted to the optical fiber can be ascertained. The method and apparatus of the present invention enable eccentricity to be measured in such a way that this measurement can be utilized to determine the amount of spin imparted to an optical fiber as the optical fiber is was being drawn, although the eccentricity measurement need not be used to determine the amount of spin in the fiber. The measured eccentricity may be used for other purposes as well.

In manufacturing optical fiber, various manufacturing effects leave the core of the fiber slightly offset from the center of the cladding. This core offset is commonly known as "core-clad concentricity error", or more briefly, "eccentricity". The eccentricity in modern fibers is typically on the order of 0.05 micrometers ($\mu$m)–0.5 $\mu$m. In accordance with the present invention, it has been observed that when a spun fiber is viewed from a position transverse to the length of the fiber, the core of the fiber follows a helical path that directly records the spin imparted to the fiber while it was being drawn. In accordance with the present invention, it has been determined that by viewing the fiber from a position generally transverse to the length of the fiber (i.e., transversely), the projected magnitude of the eccentricity of the fiber core as a function of position along the length of the fiber (hereinafter referred to as "transverse eccentricity") can be determined with an accuracy better than 0.05 $\mu$m. By analyzing the change in transverse eccentricity with length, the amount of spin in the fiber can be determined. For example, by looking at the transverse eccentricity in a single plane, the negative and positive excursions of transverse eccentricity can be used to determine the number of spins imparted to the fiber over a length of the fiber. Essentially, the number of negative excursions corresponds to the number of spins, as do the number of positive excursions.

Alternatively, by looking at the transverse eccentricity from two different directions, which preferably (but not necessarily) are approximately 90 degrees apart from one another and generally transverse to the length of the fiber, the detailed variation of spin along the length of the fiber can be reconstructed. The detailed variation of spin along the length of the fiber can also be determined directly by rotating either the fiber or the sensor to find and record the angle of greatest transverse eccentricity as a function of position along the fiber. The phrase "detailed variation", as that phrase is used herein, is intended to denote the spin velocity, i.e., both the spin rate and direction of spin along the length of fiber. It should be noted that this detailed variation information may also be obtained using non-orthogonal views with suitable processing to account for some known relationship between the views.

In accordance with the preferred embodiment, the system comprises a light source, at least one optical sensor, first processing logic and second processing logic. The optical sensor receives light projected by the light source through the optical fiber that impinges on the optical sensor. The light that impinges on the optical sensor constitutes a projection of a view of the fiber from a direction transverse to the length of the fiber. The optical sensor generates electrical signals in response to the light that impinging on it. The first processing logic receives the electrical signals and is configured to process the electrical signals to determine the transverse eccentricity of the optical fiber along the length of fiber being tested. The second processing logic is configured to process the determined transverse eccentricity to obtain the amount of spin imparted to the optical fiber.

Because the present invention enables the spin to be easily and quickly determined, the present invention is particularly well suited for automation. These and other features and advantages of the present invention will become apparent from the following description, drawings and claims.

DETAILED DESCRIPTION OF THE PREFERRED EMBODIMENTS

In accordance with the present invention, it has been determined that the spin in the fiber can be determined from the eccentricity of the fiber. The present invention provides a system for measuring the eccentricity imparted to an optical fiber. Preferably, the system is also configured to utilize the eccentricity measurement to determine the amount of spin imparted to an optical fiber as the optical fiber was being drawn. In accordance with the present invention, it has been determined that by viewing the fiber from its side (i.e., transversely), the eccentricity of the fiber as a function of position along the length of the fiber (hereinafter referred to as "transverse eccentricity") can be determined. The amount of spin in the fiber can then be determined from the transverse eccentricity.

Figure 1:
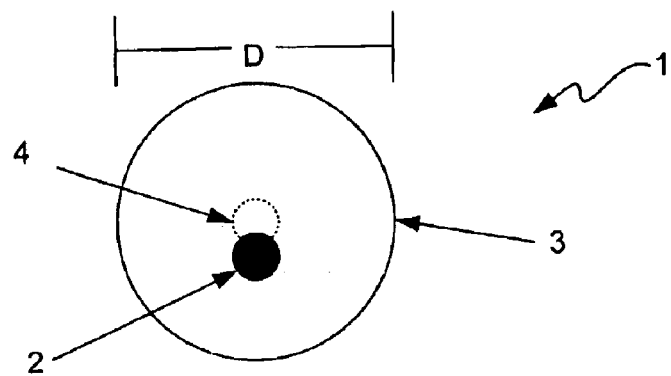
FIG. 1 is an end view of a spun fiber having a certain amount of core-cladding eccentricity.

FIG. 1 is an end view of an optical fiber 1 having a core 2 and a cladding 3 that surrounds the core 2. The fiber has a diameter D, which is typically around 125 microns ($\mu$m). The center of the fiber 1 with respect to the diameter of the cladding 3 is represented by the dashed circle 4. In a spun fiber, the core 2 follows a helical path along the length of the fiber. The magnitude of the eccentricity does not change along the length of the spun fiber, but its direction does change. This can be seen from FIG. 2, which is an idealized perspective view of a length of the spun fiber 1. In this case, the fiber has been spun alternately two complete turns clockwise and two turns counter clockwise. The helical path of the core 2 along a length, L, of the fiber 1 is evident from the negatively directed and positively directed excursions of the core 2, which can be seen when viewing the spun fiber 1 from the side (i.e., from some transverse position with respect to the length of the fiber). The number of excursions between positive and negative eccentricity of the spun fiber 1 over some length L directly corresponds to the number of turns in the helix over length L. Based on the number of turns counted over a particular length L of the spun fiber, the frequency at which the fiber 1 was spun can be ascertained.

It should be noted that, although the present application is discussed with respect to determining the amount of spin imparted to a fiber during the drawing process, eccentricity variations imparted to the fiber by other means may also be measured using the present invention. Therefore, although the discussion provided herein is directed to determining spin imparted to a fiber during the draw process from an eccentricity measurement, it should be understood that this is only for purposes of discussion and that the present invention is not limited to this example embodiment.

Figure 2:
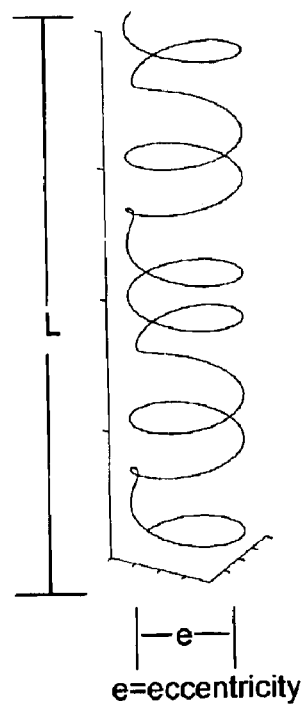
FIG. 2 is a perspective view of the path followed by the core of a spun fiber that has been spun alternately two complete turns clockwise and two turns counter clockwise during the draw.
Figure 3A:
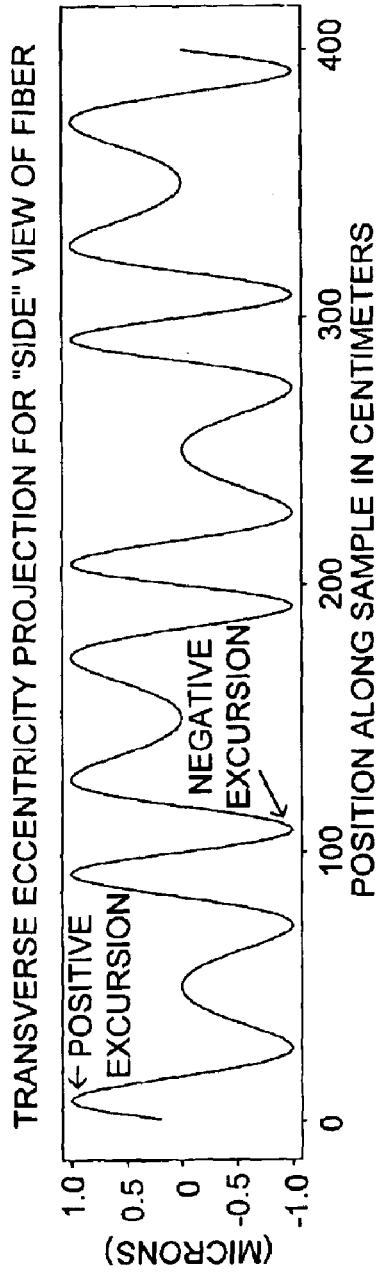
FIG. 3A is a graph of the transverse eccentricity of the core shown in FIG. 2 viewed from a side orientation.
Figure 3B:
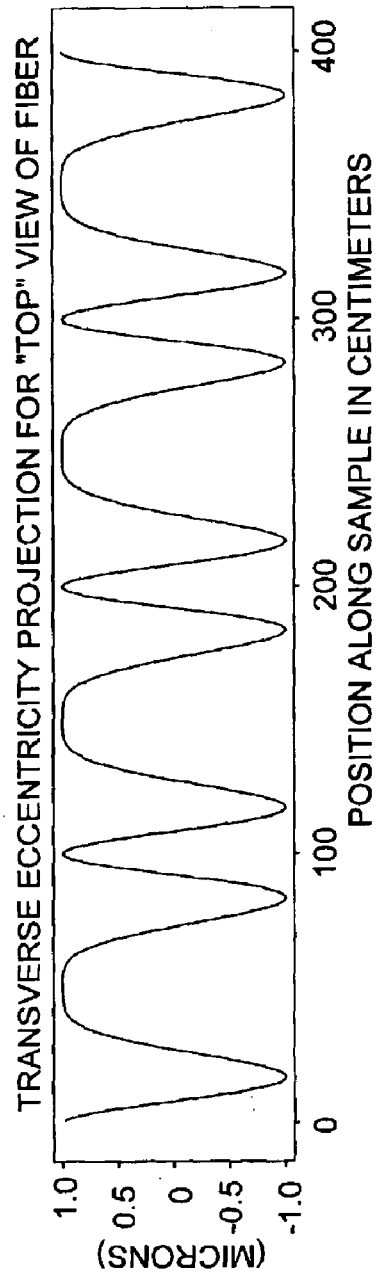
FIG. 3B is a graph of the transverse eccentricity of the core shown in FIG. 2 viewed from a top orientation that is approximately 90 degrees apart from the side orientation associated with FIG. 3A.

FIG. 3A is a graph of the transverse eccentricity of the core 2 shown in FIG. 2 viewed from a side orientation. FIG. 3B is a graph of the transverse eccentricity of the core 2 shown in FIG. 2 viewed from a top orientation, which is 90 degrees separated from the side orientation of FIG. 3A. The transverse eccentricity of the core 2 can be obtained from either view by determining either the number of positive excursions of the transverse eccentricity or the number of negative excursions of the transverse eccentricity. It has also been determined in accordance with the present invention that by combining data from both the side view and the top view, the detailed variation of the spin that was imposed on the fiber during the draw process can be determined.

Figure 4:
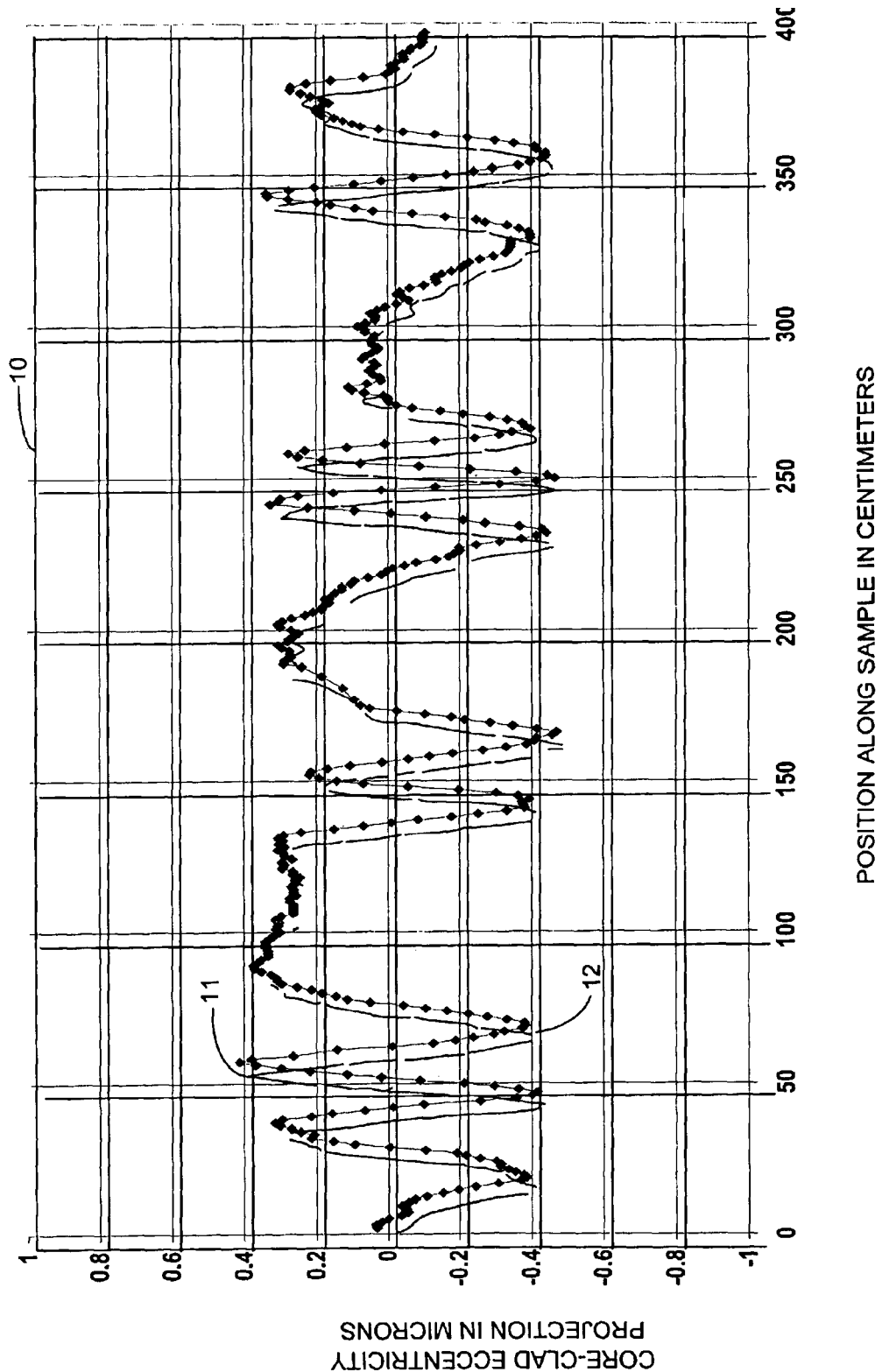
FIG. 4 is a graph having a plot of data points that represent transverse eccentricity as a function of position along the length of a portion of fiber.

FIG. 4 is a graph 10 containing data points that together constitute a plot of a projection of transverse eccentricity as a function of position along a length L of the spun fiber 1. FIG. 4 corresponds to an example of an actual test that was performed using the system of the present invention, which is described below with reference to FIG. 5. In this example, the length L of fiber utilized was 4 meters and 400 data points were obtained, which means that the interval between data points was 1 cm. By counting either the number of positive peaks 11 or the number of negative peaks 12 in the projection, the amount of spin imposed on the fiber during fabrication was determined.

The positive peaks generally are determined by analyzing the values of adjacent data points to determine a pattern of data points having values that increase as length increases followed by a pattern of data points having values that decrease as length increases. The maximum data value in this pattern is determined to correspond to a positive peak. The negative peaks can be determined in a similar manner. The negative peaks generally are determined by analyzing the values of adjacent data points to determine a pattern of data points having values that decrease as length increases followed by a pattern of data points having values that increase as length increases. The minimum data value in this pattern is determined to correspond to a negative peak. Depending on the preciseness of the imaging system used to obtain the data points, it is possible to detect false maximum or false minimum data point values, which could result in the determination as to the number of spins possibly not being as precise as it could be.

To ensure the preciseness of the calculations, the data values can be processed in accordance with interpolation and/or estimation algorithms that eliminate or reduce such errors. Known algorithms such as a least squares algorithm, a nearest neighbor algorithm and/or various curve-fitting algorithms are suitable for this purpose. Although numerous intervals may be chosen at which to view the spun fiber 1, typical values would be 0.5 cm, 1.0 cm, etc. Of course, the present invention is not limited to any particular intervals or the manner in which they are chosen. Generally, the preciseness of the calculations will increase as the number of data points obtained over the length L increases. A typical length L of spun fiber 1 that is viewed may be, for example, 2 to 12 meters, although the present invention is not limited to any particular length. Again, various lengths may be selected. These selections preferably are made in such a way that spin can be precisely determined quickly and efficiently in an automated system.

In order to ensure that the data point measurements are taken from the same angular position, the fiber 1 preferably is prevented from rotating as the data point measurements are obtained over the length L of the spun fiber 1. Otherwise, the helical projection of the core along the length L of the spun fiber may become distorted, thereby resulting in faulty measurements and calculations. Preventing the fiber from rotating can be accomplished by using a variety of mechanisms. For example, the spun fiber 1 may be arranged in a number of free hanging loops, or catenaries (not shown). In this case, the spun fiber 1 would be draped over holding fixtures that gently hold and wipe the fiber 1. The loops would allow an operator to visually detect any twist in the fiber 1 and remove it. An alternative to providing a configuration that would prevent the fiber from rotating would be to utilize information relating to the mechanical twist in the fiber during processing in order to account for the twist when making the necessary calculations.

Figure 5:
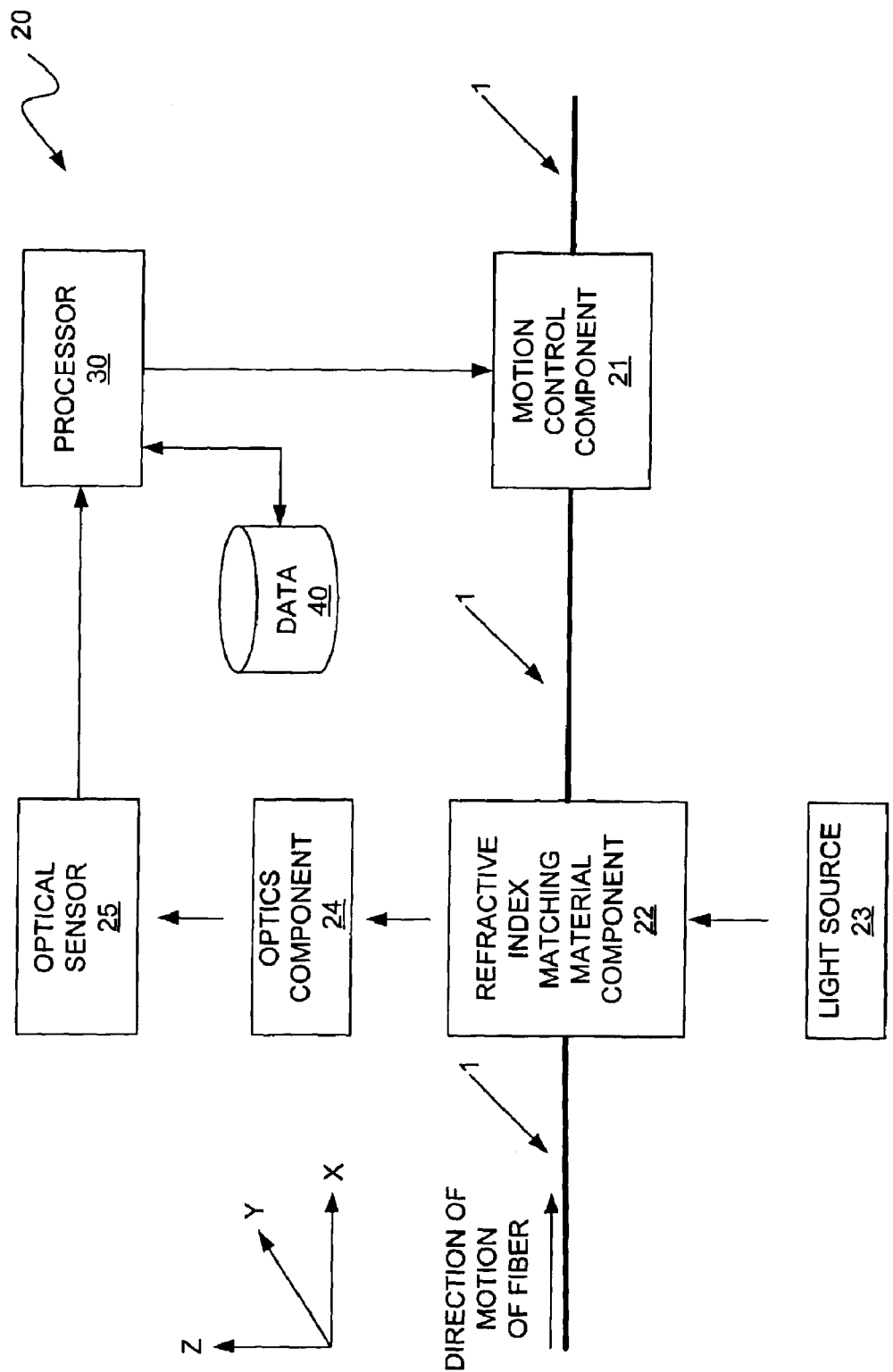
FIG. 5 is a block diagram of the system of the present invention in accordance with an example embodiment.

The foregoing description of the example embodiments of the present invention assumes that the fiber, as opposed to the imaging components, is being moved with fixed angular orientation as the measurements are obtained. It is preferable to move the fiber as the measurements are obtained because, for reasons that will become apparent from the description of FIG. 5 below, moving the imaging components while keeping the fiber 1 in a fixed position may hinder automation of the present invention. However, as will be understood by those skilled in the art, in view of the description provided herein, all that is necessary is that the relative motions and orientations between the imaging components and the fiber be known, regardless of how that motion is achieved. FIG. 5 is a block diagram of the system 20 of the present invention in accordance with an example embodiment. The fiber 1 is moved in the X-direction by a motion control component 21 that grips and pulls the fiber 1 through the system 20, which may comprise, for example, a stepper motor and one or more sheaves (not shown). A processor 30 is programmed to send signals to the motion control component 21 to cause the motion control component 21 to increment the position of the fiber 1 in the X-direction in accordance with the selected intervals. As the fiber 1 is incremented, a portion of the fiber passes through a refractive index matching material component 22. A light source 23 is positioned to project light through component 22 and through a portion of the fiber 1 being imaged. The refractive index matching material component 22 ensures that the refractive index outside of the fiber 1 has an appropriate value, so as to prevent unwanted reflection and/or refraction of the light. A refractive index matching oil may be used for this purpose.

As light passes through the portion of the fiber being imaged, an optics component 24, which may comprise one or more lenses and/or other optical components, focuses the light onto an optical sensor 25, which may be, for example, a charge coupled device (CCD) array. The optical sensor 25 produces electrical signals in response to the light that impinges thereon and outputs the electrical signals to the processor 30. The processor 30 processes the electrical signals in the manner discussed above to determine the projected transverse eccentricity at the location of the fiber 1 being imaged. The processor 30 generates a record of the projected transverse eccentricity over the length of the fiber 1 and then processes the record to determine the number of spins imparted to the fiber 1. As stated above, this may be accomplished by determining the number of positive excursions or the number of negative excursions indicated by the data over the length of the fiber 1. Either of these numbers corresponds to the number of spins in the fiber over the length L of fiber used.

The processor 30 may be in communication with a memory device 40 in which the records of data values are stored for later processing. The memory device 40 may also store programs that are used by the processor 30 to perform the aforementioned functions. In this sense, the processor 30 and the memory device 40 can be thought of as logic for performing the aforementioned tasks. Specifically, the processor 30 and memory device 40 can be thought of as first logic configured to perform a first algorithm stored in memory device 40, which, when executed by the processor 30 generates the record of transverse eccentricity as a function of position along the length of fiber being tested. Similarly, the processor 30 and memory device 40 can be thought of as second logic configured to perform a second algorithm stored in memory device 40, which, when executed by the processor 30 analyzes the record of transverse eccentricity data stored in the memory device 40 to determine the spin imparted to the length of fiber being tested.

It should be noted that these algorithms may be separate routines of a single program or they may be separate programs. As indicated above, if a fiber that is drawn with the appropriate spin imparted to it, the fast and slow axes are substantially eliminated and all light travels with substantially the same velocity. This, in turn, reduces or eliminates PMD. By determining the amount of spin that is being imparted to the fiber, proper operation of the production facility equipment, such as the drawing tower, can be insured. As well, frequent testing for the amount of spin can enable malfunctions of equipment to be detected at the earliest stages, thereby preventing fiber from being wasted due to the fiber being improperly spun as it was drawn.

It should be noted that it is not necessary that the light projected through the optical fiber and focused onto the optical sensor form a perfectly transverse projection of the optical fiber on the optical sensor. Those skilled in the art will understand, in view of the present disclosure, that the positions of the light source and optical sensor can be varied such that the view received by the optical sensor is not precisely transverse to the length of the fiber 1. In such cases, the electrical signals generated by the optical sensor can be processed to reconstruct a transverse view, which can then be used to obtain the amount of spin. Therefore, although the light source and optical sensor are shown in FIG. 5 as being transverse to the length of the fiber 1, this geometry is not necessary. Also, the optics component can be designed to direct the light that passes through the fiber in virtually any direction. Similarly, an optical component could be used in conjunction with the light source to project the light onto the fiber 1 in the desired manner.

Figure 6:
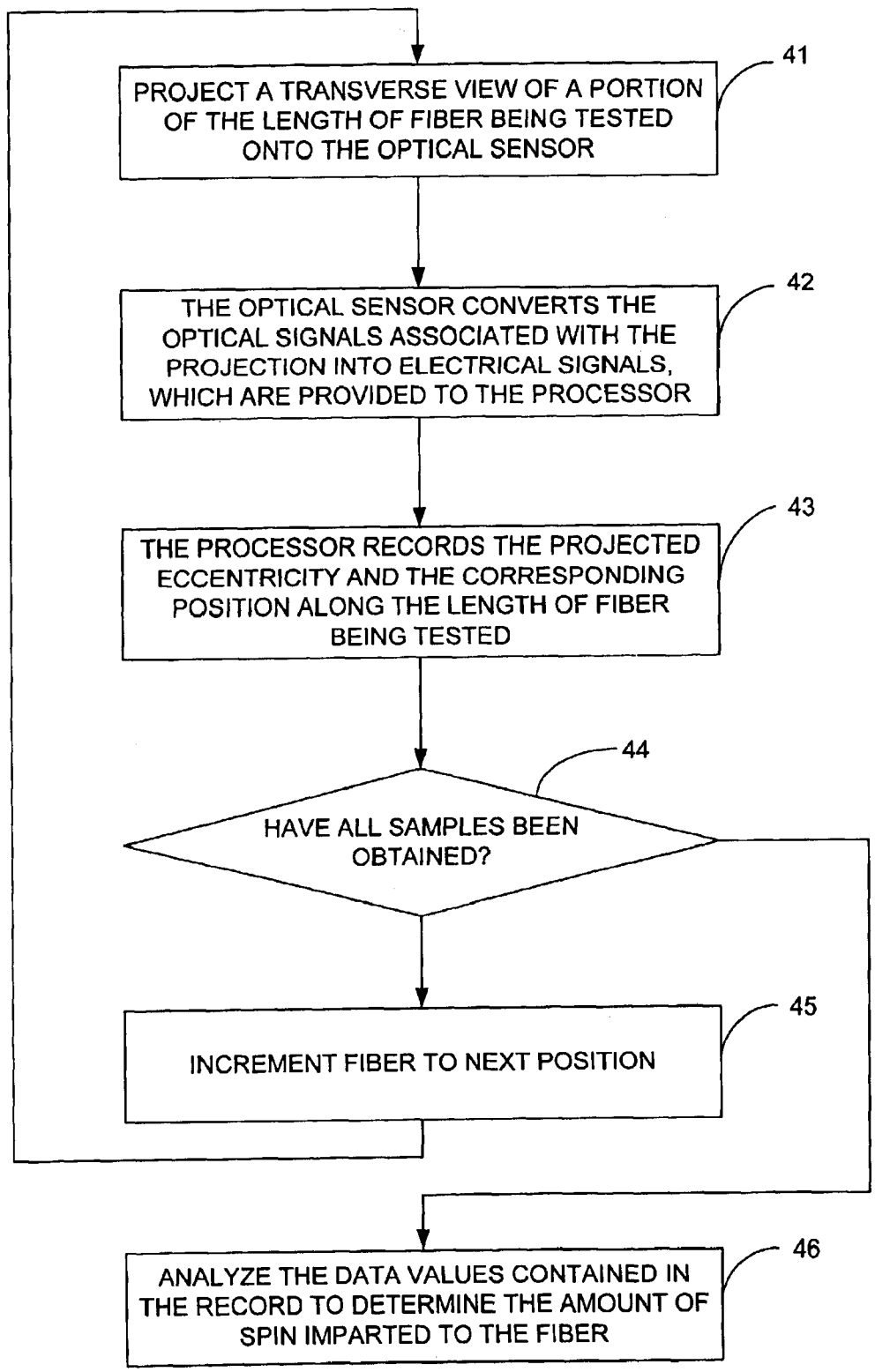
FIG. 6 is a flow chart illustrating the method of the present invention in accordance with an example embodiment.

FIG. 6 is a flow chart illustrating the method of the present invention in accordance with an example embodiment. As indicated by block 41, light projected through the optical fiber forms a projection of a side, or transverse, view of the eccentricity of a portion of the optical fiber on the optical sensor. The optical sensor converts the optical signals into electrical signals, which are provided to the processor, as indicated by block 42. The processor then records the transverse eccentricity and the position along the length of the fiber, as indicated by block 43. A determination is then made as to whether all of the samples have been obtained, as indicated by decision block 44. If not, the fiber is incrementally moved and the next position along the length of the fiber is imaged, as indicated by block 45, and the process returns to the step represented by block 41. The process represented by blocks 41–45 is repeated until a record of transverse eccentricity as a function of position has been obtained for the selected length of fiber. Once the record has been generated, the processor analyzes the data values contained in the record to determine the number of spins for the given length of fiber being tested. This step is represented by block 46.

It should also be noted that it is not necessary that step 46 be performed by a processor or other computational device. The helical path along the length of the fiber being tested can be seen by a human operator using a microscope. Therefore, the amount of spin in the fiber could be determined by a human operator who counts either the positive or negative transverse eccentricity excursions. Also, a plot such as that shown in FIG. 4 could be generated and displayed and/or printed out and a human operator could determine the number of spins in the fiber from the plot. Therefore, although step 46 preferably is performed by a computational device that can generate feedback signals in accordance with the amount of spin it determines, this is to facilitate automation and to reduce the possibility of human error and is not necessary to the present invention.

In the example embodiments described above, transverse eccentricity was measured at only one transverse orientation, and only for the purpose of determining the number of spins that occur along a given length of fiber. Many other options are within the scope of this invention, and generally will depend on the nature of the information that is being sought. For example, data from one transverse orientation can be analyzed by looking at the variation of the distance between successive zero crossings of the transverse eccentricity to yield information about the variation of spin rate with length along a fiber. In addition, as stated above, by combining transverse eccentricity data at two orientations, the detailed variation of spin along the length of a fiber can be obtained. The orientations, or view points, at which the eccentricity data is obtained are preferably, but not necessarily, orthogonal to one another. As indicated above, when data is obtained from non-orthogonal view points, knowledge of the positions of two non-orthogonal view points can be used to ensure that the eccentricity measurements are processed in a way that accounts for the non-orthogonal positioning.

It should be noted that the above-described embodiments of the present invention are example embodiments and that the present invention is not limited to these particular embodiments. Many variations and modifications may be made to the above-described embodiments. All such modifications and variations are within the scope of present invention. For example, although a processor 30 is shown and described as executing software for performing the eccentricity projection and the spin computations, these calculations could be performed by solely in hardware, in a combination of hardware and software, in firmware, in a field programmable logic array (FPGA), etc. The system 20 shown in FIG. 5 can be implemented in a variety of ways using a variety of components. It should also be noted that the system of the present invention can be utilized to determine the amount of spin that was imparted to a coated or uncoated fiber. It also is not necessary that the refractive index matching component 22 be used, although its use is preferred. Those skilled in the art will understand the manner in which other variations to the embodiments described above can be made while remaining within the scope of the present invention.

What is claimed is:

1. An apparatus for measuring eccentricity in an optical fiber, the apparatus comprising an optical sensor for obtaining a projection view of the fiber from at least one position that is substantially transverse to the length of the fiber, the view corresponding to a transverse eccentricity of the fiber along the length of fiber, and a processor coupled to the optical sensor and including processing logic configured to process the projection view to determine said transverse eccentricity, wherein the processing logic counts at least one of a number of positive excursions and a number of negative excursions of the transverse eccentricity and determines the amount at spin imparted to the fiber along said length from a total number of excursions of the transverse eccentricity along said length.

2. The apparatus of claim 1, wherein the processing logic includes logic that is configured to determine an amount of spin imparted to the fiber from the determined transverse eccentricity.

3. The apparatus of claim 2, wherein the spin was imparted to the fiber during a drawing process when the fiber was being manufactured.

4. The apparatus of claim 2, further comprising:
a light source that produces light that is projected onto a length of the optical fiber,
wherein the optical sensor receives the light projected by the light source that passes through the optical fiber, the projected light constituting said projection view of the fiber from a position that is substantially transverse with respect to the length of fiber, the optical sensor generating electrical signals that correspond to the projection view, the electrical signals corresponding to the signals that the processing logic processes to determine said amount of spin.

5. The apparatus of claim 4, wherein the processing logic includes first processing logic and second processing logic, the first processing logic being configured to receive and process the electrical signals to determine the transverse eccentricity, the second processing logic being configured to process the determined transverse eccentricity to obtain the amount of spin that was imparted to the optical fiber along the length of the optical fiber as the fiber was being drawn.

6. The apparatus of claim 5, wherein the first processing logic executes an algorithm that generates a record of the transverse eccentricity of the optical fiber along said length, the record comprising a plurality of entries, each entry including a transverse eccentricity value and a position along said length to which the transverse eccentricity value corresponds.

7. The apparatus of claim 5, wherein the second processing logic executes an algorithm that processes the determined transverse eccentricity to determine the amount of spin imparted to the fiber.

8. The apparatus of claim 7, wherein when the processor executes the algorithm, the processor counts a number of positive maximum excursions of the transverse eccentricity and determines the amount of spin imparted to the fiber along said length from a total number of positive maximum excursions of the transverse eccentricity along said length.

9. The apparatus of claim 7, wherein when the processor executes the algorithm, the processor counts a number of negative minimum excursions of the transverse eccentricity and determines the amount of spin imparted to the fiber along said length from a total number of negative minimum excursions of the transverse eccentricity along said length.

10. A system for determining an amount of spin imparted to an optical fiber as the optical fiber was being drawn, the system comprising:
a light source that produces light that is projected onto a length of the optical fiber;
an optical sensor that receives the light projected by the light source that passes through the optical fiber, the projected light constituting a projection view of the fiber from a position that is substantially transverse with respect to the length of fiber, the view corresponding to a transverse eccentricity of the fiber along the length of fiber, the optical sensor generating electrical signals that correspond to the projection view; and
a processor having first end second logic,
the first processing logic being configured to receive and process the electrical signals to determine said transverse eccentricity, and
the second processing logic being configured to process the determined transverse eccentricity to obtain the amount of spin imparted to the optical fiber along the length of the optical fiber, wherein the second processing logic counts at least one of a number of positive excursions and a number of negative excursions of the transverse eccentricity and determines the amount of spin imparted to the fiber along said length from a total number of excursions of the transverse eccentricity along said length.

11. The system of claim 10, wherein the first processing logic executes an algorithm that generates a record of the transverse eccentricity of the optical fiber along said length, the record comprising a plurality of entries, each entry including a transverse eccentricity value and a position along said length to which the transverse eccentricity value corresponds.

12. The system of claim 10, wherein the second processing logic executes an algorithm that processes the determined transverse eccentricity to determine the amount of spin imparted to the fiber.

13. The system of claim 12, wherein when the processor executes the algorithm, the processor counts a number of positive maximum excursions of the transverse eccentricity and determines the amount of spin imparted to the fiber along said length from a total number of positive maximum excursions of the transverse eccentricity along said length.

14. The system of claim 12, wherein when the processor executes the algorithm, the processor counts a number of negative minimum excursions of the transverse eccentricity and determines the amount of spin imparted to the fiber along said length from a total number of negative minimum excursions of the transverse eccentricity along said length.

15. A method for determining an amount of spin imparted to an optical fiber as the optical fiber was being drawn, the method comprising the steps of:
obtaining a projection view of the fiber from a position that is substantially transverse to the length of the fiber, the view corresponding to a transverse eccentricity of the fiber along the length of fiber; and
processing signals associated with the projection view to determine said amount of spin, wherein the processing step counts at least one of a number of positive excursions and a number of negative excursions of the transverse eccentricity and determines the amount of spin imparted to the fiber along said length from a total number of excursions of the transverse eccentricity along said length.

16. The method of claim 15, wherein the substantially transverse view corresponds to a transverse eccentricity of the length of fiber, the processing step including processing the signals associated with the projection view with processing logic to determine the transverse eccentricity associated and determining said amount of spin from the determined transverse eccentricity.

17. The method of claim 16, wherein the processor includes first processing logic and second processing logic, the first processing logic being configured to receive and process the electrical signals to determine said transverse eccentricity, the second processing logic being configured to process the determined transverse eccentricity to obtain the amount of spin imparted to the optical fiber along the length of the optical fiber.

18. The method of claim 17, wherein the first processing logic executes an algorithm that generates a record of the transverse eccentricity of the optical fiber along said length, the record comprising a plurality of entries, each entry including a transverse eccentricity value and a position along said length to which the transverse eccentricity value corresponds.

19. The method of claim 17, wherein the second processing logic executes an algorithm that processes the determined transverse eccentricity to determine the amount of spin imparted to the fiber.

20. The method of claim 19, wherein when the processor executes the algorithm, the processor counts a number of positive maximum excursions of the transverse eccentricity and determines the amount of spin imparted to the fiber along said length from a total number of positive maximum excursions of the transverse eccentricity along said length.

21. The method of claim 15, wherein the step of obtaining the projection view includes the steps of:

projecting light from a light source onto a length of the optical fiber; and capturing a projection view of said length with an optical sensor the projection view corresponding to a view of the fiber from a position that is substantially transverse with respect to said length, the optical sensor generating electrical signals that correspond to the projection view, the electrical signals corresponding to the signals that are processed by a processor to determine said amount of spin.

* * * * *